US009375001B1

(12) United States Patent
Yang et al.

(10) Patent No.: US 9,375,001 B1
(45) Date of Patent: Jun. 28, 2016

(54) GRANULAR FLY BAIT

(71) Applicant: Wellmark International, Schaumburg, IL (US)

(72) Inventors: Kim W. Yang, Dallas, TX (US);
William B. Warner, Chandler, AZ (US);
Doug Vangundy, Dallas, TX (US);
Tracy McFadden, Dallas, TX (US);
Richard Moorman, Dallas, TX (US);
I-Hsiung Wang, Dallas, TX (US)

(73) Assignee: WELLMARK INTERNATIONAL, Schaumburg, IL (US)

( * ) Notice: Subject to any disclaimer, the term of this patent is extended or adjusted under 35 U.S.C. 154(b) by 0 days.

(21) Appl. No.: 13/781,235

(22) Filed: Feb. 28, 2013

Related U.S. Application Data

(60) Provisional application No. 61/637,217, filed on Apr. 23, 2012.

(51) Int. Cl.
*A01N 27/00* (2006.01)
*A01N 43/08* (2006.01)
*A01N 43/40* (2006.01)
*A01N 25/26* (2006.01)
*A01N 43/50* (2006.01)

(52) U.S. Cl.
CPC ............... *A01N 43/50* (2013.01); *A01N 25/26* (2013.01); *A01N 27/00* (2013.01); *A01N 43/08* (2013.01); *A01N 43/40* (2013.01)

(58) Field of Classification Search
CPC ............................ A01N 25/006; A01N 25/12
See application file for complete search history.

(56) References Cited

U.S. PATENT DOCUMENTS

| 4,369,176 A * | 1/1983 | Ott ................................... 424/84 |
| 4,449,987 A | 5/1984 | Lindauer |
| 4,981,697 A * | 1/1991 | Miller et al. ....................... 426/2 |
| 5,008,107 A | 4/1991 | Warner |
| 5,021,237 A | 6/1991 | Bruey |
| 5,342,547 A | 8/1994 | Konya et al. |
| 5,720,951 A | 2/1998 | Baker |
| 5,720,968 A | 2/1998 | Shasha |
| 6,245,327 B1 | 6/2001 | Faehl |
| 2002/0010156 A1* | 1/2002 | Kennedy et al. ................ 514/65 |
| 2004/0208953 A1 | 10/2004 | Heath |
| 2005/0063903 A1 | 3/2005 | Zeligs |
| 2005/0142160 A1 | 6/2005 | Hiscox |
| 2008/0089857 A1 | 4/2008 | Hutchet et al. |
| 2009/0221662 A1 | 9/2009 | Gutsmann |
| 2009/0304624 A1 | 12/2009 | Gutsmann |
| 2010/0028295 A1 | 2/2010 | Taranta et al. |
| 2010/0158965 A1 | 6/2010 | Beitzel et al. |
| 2011/0072711 A1 | 3/2011 | Black et al. |
| 2012/0270944 A1 | 10/2012 | Zhang et al. |

FOREIGN PATENT DOCUMENTS

| JP | 2012067015 A * | 4/2012 | ............ A01N 25/08 |
| WO | 2006/124507 A1 | 11/2006 | |
| WO | 2009/150254 | 12/2009 | |
| WO | 2010/025454 A2 | 3/2010 | |
| WO | 2012/095444 A2 | 7/2012 | |

OTHER PUBLICATIONS

Keller et al. Jour. Econ. Ent., 1955, 48(5), 563-565, abstract only.*

* cited by examiner

*Primary Examiner* — Mina Haghighatian
*Assistant Examiner* — Erin Hirt
(74) *Attorney, Agent, or Firm* — Kilpatrick Townsend & Stockton LLP

(57) ABSTRACT

The present invention provides insecticidal compositions for killing flies. The composition comprises a core material, a sugar layer comprising a supersaturated solution of sugar and a toxicant, which binds the core material and is dried on the core material.

24 Claims, 1 Drawing Sheet

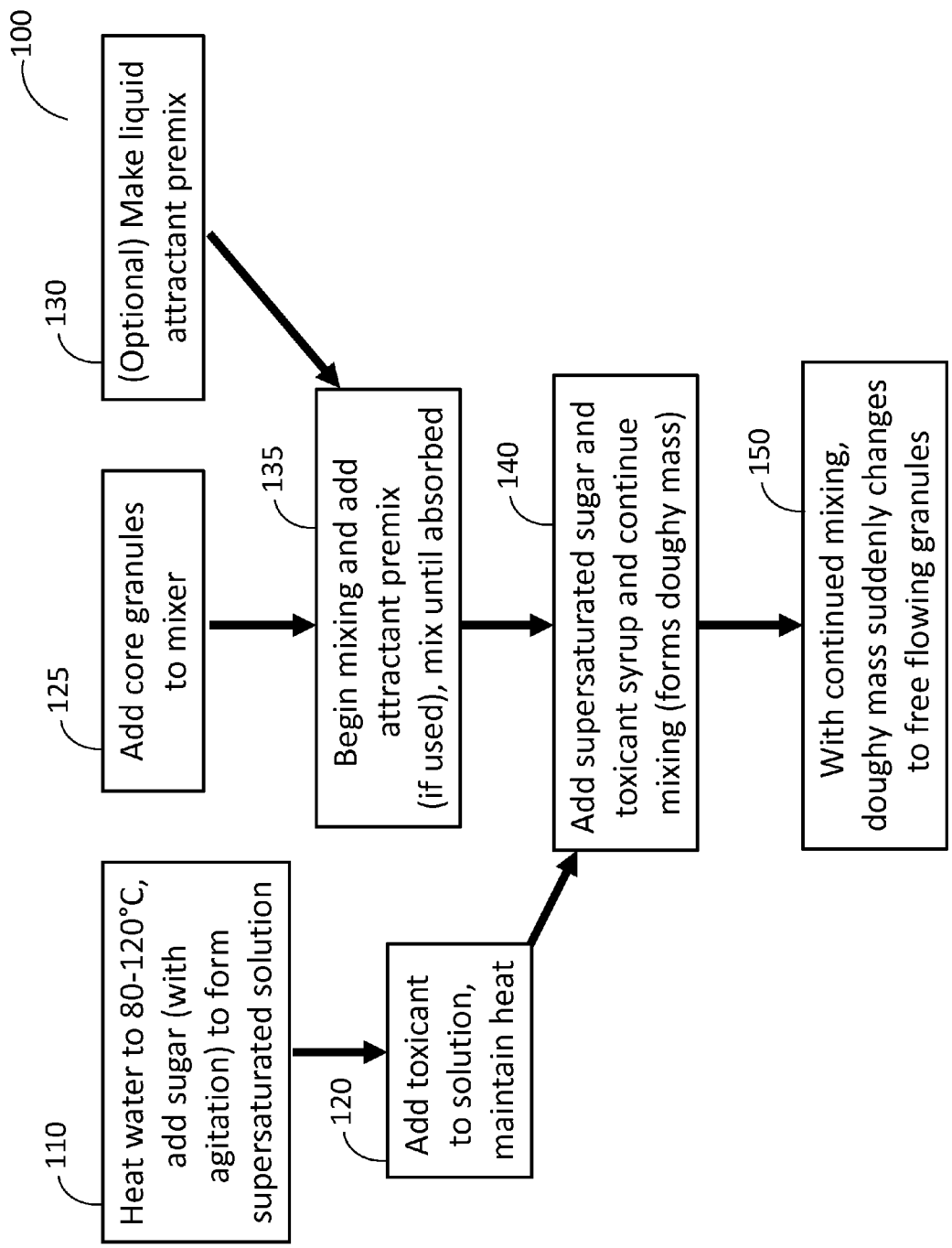

GRANULAR FLY BAIT

The present application claims priority to U.S. Provisional Patent Application No. 61/637,217, filed Apr. 23, 2012, the disclosure of which is hereby incorporated by reference in its entirety for all purposes.

FIELD OF THE INVENTION

The present invention relates generally to insecticidal compositions. In particular, the present invention provides compositions of insecticides useful to control or kill flies.

BACKGROUND OF THE INVENTION

The house fly, *Musca domestica* Linnaeus, is a well-known pest of both farms and homes. This species is normally found in association with humans or activities of humans, and is the most common species found on cattle, hog and poultry farms, horse stables, and ranches. In addition to being a nuisance, flies can transport disease-causing microorganisms. Moreover, excessive fly populations are obnoxious to farm workers.

Flies develop and congregate in large numbers in livestock areas, such as poultry manure under caged hens. This is a serious problem requiring control. The control of *Musca domestica* is vital to human health and comfort in many areas of the world. The insect is an annoyance and can transmit various pathogens that can be harmful to humans and animals.

Various methods have been developed to control flies, including insecticidal sprays, traps, insecticidal baits, larvicides, and combinations thereof to directly or indirectly suppress adult fly densities. Common measures to directly control adult flies include the use of traps or insecticidal baits, which employ attractants to draw flies from a distance to a point source where they are trapped or ingest a toxicant. Fly traps may be useful in some fly control programs if enough traps are used, and if they are placed correctly. Insecticidal baits provide a more convenient means of fly control because they do not require a discrete physical device to be handled, and the amount applied may be easily scaled to the intended area of control. Insecticidal baits typically combine a toxicant (insecticide), an attractant, and a feeding adjuvant such as sugar.

Although such baits are known in the art, there exists a need for better and more efficacious fly baits. The current invention satisfies this and other needs.

BRIEF SUMMARY OF THE INVENTION

The present invention provides compositions, methods of using the compositions, and methods of making the composition, wherein the compositions are useful to control or kill flies. As such, in one embodiment, the present invention provides a composition comprising, consisting essentially of, or consisting of a supersaturated sugar layer comprising a toxicant applied over an inert core. In certain aspects, the composition further comprises an attractant.

In certain aspects, the attractant is applied to the inert core prior to a coating having a toxicant such that the inert core protects the attractant from further processing steps. In certain other aspects, the coating protects the attractant from premature loss during handling. Advantageously, the toxicant and attractants are substantially separated during the coating phase. Suitable attractants include a pheromone or multiple pheromones, a feeding attractant or attractants, and a combination thereof.

In another embodiment, the present invention provides a composition for killing flies, comprising, consisting essentially of, or consisting of:
  an inert core material; and
  a sugar layer comprising a supersaturated solution of sugar and a toxicant, which binds to the core material and is dried on the core material.

In another embodiment, the present invention provides a method for controlling flies, the method comprising, consisting essentially of, or consisting of:
  applying a composition comprising:
  an inert core material; and
  a sugar layer comprising a supersaturated solution of sugar and a toxicant, which binds to the core material and is dried on the core material, to a locus where fly control is needed or expected to be needed.

In yet another embodiment, the present invention provides a method for controlling flies comprising, consisting essentially of, or consisting of, applying the composition of the present invention to a locus where fly control is needed or expected to be needed. Flies can be filth flies such as house flies (*Musca domestica* Linneaus), bazaar flies (*Musca sorbens* (Weidemann)), eye gnats (*Hippelates* species), blow flies (Calliphoridae), little house flies (*Fannia* species), flesh flies (Sarcophagidae), and pomace flies (*Drosophila* species). The locus is a fly-infested location. Alternatively, the location is expected to be fly-infested and/or an area adjacent thereto. More particularly, the locus is a farm, a cattle facility, an animal breeding facility, a food processing facility, a restaurant, a recreational park, a residential area or a residential building.

These and other objects, aspects and embodiments will become more apparent with the detailed description and FIGURE that follow.

BRIEF DESCRIPTION OF THE DRAWINGS

The FIGURE is a flow diagram for one embodiment of a method of making a composition of the present invention.

DETAILED DESCRIPTION OF THE INVENTION

I. Definitions

The term "about" as used herein, includes a close, but imprecise quantity of a value. For example, in certain instances the term about includes as much as 5%, 6%, 7%, 8%, 9%, or 10% higher, or as much as 5%, 6%, 7%, 8%, 9%, or 10% lower than the explicit value given. For example, "about 10" includes the range of values from 9.5 to 10.5.

When "about" is applied to the beginning of a numerical range, it applies to both ends of the range. Thus, "from about 5 to 20%" is equivalent to "from about 5% to about 20%." When "about" is applied to the first value of a set of values, it applies to all values in that set. Thus, "about 7, 9, or 11%" is equivalent to "about 7%, about 9%, or about 11%."

The term "inert core material" includes any material that is a carrier preferably having a granular structure upon which a coating may be applied. When using an attractant, porous cores may be preferred to absorb the attractant and limit its interaction with the coating. A wide variety of inert core materials can be used in the invention including, but not limited to, cellulose granules, ground nut hulls such as ground walnut halls, cellulose granules (recycled paper or other), lignin granules, sand, clay granules, polymer (plastic) granules, saw dust, a grain, a seed, millet, milo, oat bran, corn part, crack rice, crack wheat, couscous, *quinoa*, a plant part, and steel cut grain; seed such as a chia seed, a sesame seed, a flax seed, and an amaranth seed.

The term "toxicant" or "insecticide" includes an active chemical compound or ingredient that kills insects such as flies. Preferred toxicants are listed in Table II.

The term "locus" includes any locations where control of insects, such as flies, is needed or expected to be needed.

The term "mortality" includes death of the insects, such as flies, resulting from ingestion of the insecticide or toxicant.

II. Compositions

The present invention provides insecticidal compositions. In particular, the present invention provides compositions of insecticides useful to control or kill flies. As such, in one embodiment, the present invention provides a composition for killing flies, comprising, consisting essentially of, and consisting of:
  an inert core material; and
  a sugar layer comprising a supersaturated solution of sugar and a toxicant, which binds the core material and is dried on the core material.

Various materials are suitable for use as an inert core material. In certain instances, the core material is cellulose granules, ground nut hulls such as ground walnut halls, saw dust, clay pellets, sand, a grain, a seed, millet, milo, oat bran, corn part, crack rice, crack wheat, couscous, *quinoa*, a plant part, and steel cut grain; seed such as a chia seed, a sesame seed, a flax seed, and an amaranth seed. In other aspects, the core material is a corn part. The corn part can be for example, corn grit, corn cob grit and cracked corn. Preferably, the corn part is corn cob grit.

A sugar layer is disposed on the inert core material. Preferably, the sugar layer is a supersaturated solution of sugar. The sugar can be sucrose, fructose, lactose, honey, molasses, sorbitol, high fructose corn syrup or a combination thereof. Preferably, the sugar is sucrose. In certain instances, the supersaturated solution of sugar is between 65 to 85% weight per volume, such as 65%, 66%, 67%, 68%, 69%, 70%, 71%, 72%, 73%, 7%, 75%, 76%, 77%, 78%, 79%, 80%, 81%, 82%, 83%, 84%, or 85% by weight of sugar per weight of water. In other aspects, the supersaturated solution of sugar is between 85 to 95% or more weight per volume such as 85%, 86%, 87%, 88%, 89%, 90%, 91%, 92%, 93%, 94%, or 95%.

In certain aspects, the sugar is sucrose and the solubility of sucrose at a particular temperature is useful in obtaining a supersaturated solution. In certain instances, the sugar layer is between about 50% to about 100% weight per volume or weight/weight. The following solubilities in Table I can be used to generate solutions that contain more than the solubility amounts shown below. In other instances, the amount shown below is used.

TABLE I

Solubility of Sucrose in Water

| Temperature ° C. | Sucrose/water (wt/wt) |
|---|---|
| 50 | 2.59 |
| 55 | 2.73 |
| 60 | 2.89 |
| 65 | 3.06 |
| 70 | 3.25 |
| 75 | 3.46 |
| 80 | 3.69 |
| 85 | 3.94 |
| 90 | 4.20 |

In certain aspects, the sugar layer is between 15% to about 85% w/w of the composition. In other instances, the sugar layer is between about 25% to about 75% w/w. In other instances, the sugar layer when is about 30% to about 60%, or about 30%, 35%, 40%, 45%, 50%, 55%, or 60% w/w. For example, the sugar layer once dry is about 31%, 32%, 33%, 34%, 35%, 36%, 37%, 38%, 39% or 40% w/w of the dry weight of the composition. In other instances, the sugar layer is about 41%, 42%, 43%, 44%, 45%, 46%, 47%, 48%, 49%, 50%, 51%, 52%, 53%, 54%, 55%, 56%, 57%, 58%, 59% or 60% w/w or more of the composition.

In certain aspects, the formulations of the present invention are solid formulations. Such solid formulations can be for example, a granule, a particle, or a pellet. Preferably, the formulation is a granule. In one embodiment, the solid formulation is about 5 µm to about 5 mm in size. More preferably, the size is about 5 µm, 10 µm, 20 µm, 30 µm, 40 µm, 50 µm, 60 µm, 70 µm, 80 µm, 90 µm, 100 µm, 150 µm, 200 µm, 250 µm, 300 µm, 350 µm, 400 µm, 450 µm, 500 µm, 550 µm, 600 µm, 650 µm, 700 µm, 750 µm, 800 µm, 850 µm, 900 µm, 950 µm, 1 mm, 2 mm, 3 mm, 4 mm, or 5 mm. For example, in certain instances, the particle size is about 0.1 mm to amount 5 mm such as 0.1 mm, 0.2 mm, 0.3 mm, 0.4 mm, 0.5 mm, 0.6 mm, 0.7 mm, 0.8 mm, 0.9 mm, 1.0 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm, 3.1 mm, 3.2 mm, 3.3 mm, 3.4 mm, 3.5 mm, 3.6 mm, 3.7 mm, 3.8, 3.9 mm, 4.0 mm, 4.1 mm, 4.2 mm, 4.3 mm, 4.4 mm, 4.5 mm, 4.6 mm, 4.7 mm, 4.8 mm, 4.9 mm or 5.0 mm. In one particular aspect, the formulation is a homogenous sized granule, filtered through wire mesh, such as 4 mesh, 16 mesh or 40 mesh. In other instances, the formulation is a heterogeneous population of sized granules.

Various insecticides or toxicants are suitable for use in the present invention. Table II lists toxicants that are suitable for the present invention. In certain preferred instances, the toxicant of the present invention is one or more of the toxicants listed in Table II.

TABLE II

| No. | Chemical name (IUPAC) |
|---|---|
| 1. | mixture of ≥80% (2aE,4E,8E)-(5'S,6S,6'R,7S,11R,13S,15S,17aR,20R,20aR,20bS)-6'-[(S)-sec-butyl]-5',6,6',7,10,11,14,15,17a,20,20a,20b-dodecahydro-20,20b-dihydroxy-5',6,8,19-tetramethyl-17-oxospiro[11,15-methano-2H,13H,17H-furo[4,3,2-pq][2,6]benzodioxacyclooctadecin-13,2'-[2H]pyran]-7-yl 2,6-dideoxy-4-O-(2,6-dideoxy-3-O-methyl-α-L-arabino-hexopyranosyl)-3-O-methyl-α-L-arabino-hexopyranoside and ≤20% (2aE,4E,8E)-(5'S,6S,6'R,7S,11R,13S,15S,17aR,20R,20aR,20bS)-5',6,6',7,10,11,14,15,17a,20,20a,20b-dodecahydro-20,20b-dihydroxy-6'-isopropyl-5',6,8,19-tetramethyl-17-oxospiro[11,15-methano-2H,13H,17H-furo[4,3,2- |

TABLE II-continued

| No. | Chemical name (IUPAC) |
|---|---|
| | pq][2,6]benzodioxacyclooctadecin-13,2'-[2H]pyran]-7-yl 2,6-dideoxy-4-O-(2,6-dideoxy-3-O-methyl-α-L-arabino-hexopyranosyl)-3-O-methyl-α-L-arabino-hexopyranoside |
| 2. | (RS)-(O,S-dimethyl acetylphosphoramidothioate) |
| 3. | (E)-$N^1$-[(6-chloro-3-pyridyl)methyl]-$N^2$-cyano-$N^1$-methylacetamidine |
| 4. | S-6-chloro-2,3-dihydro-2-oxo-1,3-oxazolo[4,5-b]pyridin-3-ylmethyl O,O-dimethyl phosphorothioate |
| 5. | 2-methylbiphenyl-3-ylmethyl (1RS,3RS)-3-[(Z)-2-chloro-3,3,3-trifluoroprop-1-enyl]-2,2-dimethylcyclopropanecarboxylate |
| 6. | 4-bromo-2-(4-chlorophenyl)-1-ethoxymethyl-5-trifluoromethyl-1H-pyrrole-3-carbonitrile |
| 7. | O,O-diethyl O-3,5,6-trichloro-2-pyridyl phosphorothioate |
| 8. | (E)-1-(2-chloro-1,3-thiazol-5-ylmethyl)-3-methyl-2-nitroguanidine |
| 9. | (S)-α-cyano-3-phenoxybenzyl (1R,3R)-3-(2,2-dibromovinyl)-2,2-dimethylcyclopropanecarboxylate |
| 10. | O,O-diethyl O-2-isopropyl-6-methylpyrimidin-4-yl phosphorothioate |
| 11. | 2,2-dichlorovinyl dimethyl phosphate |
| 12. | (EZ)-(RS)-1-methyl-2-nitro-3-(tetrahydro-3-furylmethyl)guanidine |
| 13. | 2-(4-ethoxyphenyl)-2-methylpropyl 3-phenoxybenzyl ether |
| 14. | 5-amino-1-(2,6-dichloro-α,α,α-trifluoro-p-tolyl)-4-[(trifluoromethyl)sulfinyl]pyrazole-3-carbonitrile |
| 15. | 5,5-dimethylperhydropyrimidin-2-one 4-trifluoromethyl-α-(4-trifluoromethylstyryl)cinnamylidenehydrazone |
| 16. | (E)-1-(6-chloro-3-pyridylmethyl)-N-nitroimidazolidin-2-ylideneamine |
| 17. | methyl (S)-N-[7-chloro-2,3,4a,5-tetrahydro-4a-(methoxycarbonyl)indeno[1,2-e][1,3,4]oxadiazin-2-ylcarbonyl]-4-(trifluoromethoxy)carbanilate |
| 18. | diethyl (dimethoxyphosphinothioylthio)succinate |
| 19. | (EZ)-2'-[2-(4-cyanophenyl)-1-(α,α,α-trifluoro-m-tolyl)ethylidene]-4-(trifluoromethoxy)carbanilohydrazide |
| 20. | S-methyl (EZ)-N-(methylcarbamoyloxy)thioacetimidate |
| 21. | (EZ)-2-nitromethylene-1,3-thiazinane |
| 22. | 3-phenoxybenzyl (1RS,3RS;1RS,3SR)-3-(2,2-dichlorovinyl)-2,2-dimethylcyclopropanecarboxylate |
| 23. | (RS)-2-methyl-4-oxo-3-prop-2-ynylcyclopent-2-enyl (1RS,3RS;1RS,3SR)-2,2-dimethyl-3-(2-methylprop-1-enyl)cyclopropanecarboxylate |
| 24. | 2-isopropoxyphenyl methylcarbamate |
| 25. | a mixture of one or more of the following six active ingredients, extracted from *Chrysanthemum cinerariaefolium*:<br>1. (Z)-(S)-3-(but-2-enyl)-2-methyl-4-oxocyclopent-2-enyl (1R,3R)-2,2-dimethyl-3-(2-methylprop-1-enyl)cyclopropanecarboxylate<br>2. (Z)-(S)-3-(but-2-enyl)-2-methyl-4-oxocyclopent-2-enyl (E)-(1R,3R)-3-(2-methoxycarbonylprop-1-enyl)-2,2-dimethylcyclopropanecarboxylate<br>3. (Z)-(S)-2-methyl-4-oxo-3-(pent-2-enyl)cyclopent-2-enyl (1R,3R)-2,2-dimethyl-3-(2-methylprop-1-enyl)cyclopropanecarboxylate<br>4. (Z)-(S)-2-methyl-4-oxo-3-(pent-2-enyl)cyclopent-2-enyl (E)-(1R,3R)-3-(2-methoxycarbonylprop-1-enyl)-2,2-dimethylcyclopropanecarboxylate<br>5. (Z)-(S)-2-methyl-4-oxo-3-(penta-2,4-dienyl)cyclopent-2-enyl (1R,3R)-2,2-dimethyl-3-(2-methylprop-1-enyl)cyclopropanecarboxylate<br>6. (Z)-(S)-2-methyl-4-oxo-3-(penta-2,4-dienyl)cyclopent-2-enyl (E)-(1R,3R)-3-(2-methoxycarbonylprop-1-enyl)-2,2-dimethylcyclopropanecarboxylate |
| 26. | mixture of 50-90% (2R,3aS,5aR,5bS,9S,13S,14R,16aS,16bR)-2-(6-deoxy-3-O-ethyl-2,4-di-O-methyl-α-L-mannopyranosyloxy)-13-[(2R,5S,6R)-5-(dimethylamino)tetrahydro-6-methylpyran-2-yloxy]-9-ethyl-2,3,3a,4,5,5a,5b,6,9,10,11,12,13,14,16a,16b-hexadecahydro-14-methyl-1H-as-indaceno[3,2-d]oxacyclododecine-7,15-dione and 50-10% (2S,3aR,5aS,5bS,9S,13S,14R,16aS,16bS)-2-(6-deoxy-3-O-ethyl-2,4-di-O-methyl-α-L-mannopyranosyloxy)-13-[(2R,5S,6R)-5-(dimethylamino)tetrahydro-6-methylpyran-2-yloxy]-9-ethyl-2,3,3a,5b,6,9,10,11,12,13,14,16a,16b-tetradecahydro-4,14-dimethyl-1H-as-indaceno[3,2-d]oxacyclododecine-7,15-dione |
| 27. | mixture of 50-95% (2R,3aS,5aR,5bS,9S,13S,14R,16aS,16bR)-2-(6-deoxy-2,3,4-tri-O-methyl-α-L-mannopyranosyloxy)-13-(4-dimethylamino-2,3,4,6-tetradeoxy-β-D-erythropyranosyloxy)-9-ethyl-2,3,3a,5a,5b,6,7,9,10,11,12,13,14,15,16a,16b-hexadecahydro-14-methyl-1H-as-indaceno[3,2-d]oxacyclododecine-7,15-dione and 50-5% (2S,3aR,5aS,5bS,9S,13S,14R,16aS,16bS)-2-(6-deoxy-2,3,4-tri-O-methyl-α-L-mannopyranosyloxy)-13-(4-dimethylamino-2,3,4,6-tetradeoxy-β-D-erythropyranosyloxy)-9-ethyl-2,3,3a,5a,5b,6,7,9,10,11,12,13,14,15,16a,16b-hexadecahydro-4,14-dimethyl-1H-as-indaceno[3,2-d]oxacyclododecine-7,15-dione |
| 28. | (RS)-α-cyano-3-phenoxybenzyl N-(2-chloro-α,α,α-trifluoro-p-tolyl)-D-valinate |
| 29. | O,O,O',O'-tetramethyl O,O'-thiodi-p-phenylene bis(phosphorothioate) |
| 30. | N-cyclopropyl-1,3,5-triazine-2,4,6-triamine |
| 31. | 1-(4-chlorophenyl)-3-(2,6-difluorobenzoyl)urea |
| 32. | ethyl (E,E)-(RS)-3,7,11-trimethyldodeca-2,4-dienoate |
| 33. | ethyl (2E,4E,7S)-3,7,11-trimethyldodeca-2,4-dienoate |
| 34. | prop-2-ynyl (E,E)-(RS)-3,7,11-trimethyldodeca-2,4-dienoate |
| 35. | isopropyl (E,E)-(RS)-11-methoxy-3,7,11-trimethyldodeca-2,4-dienoate |
| 36. | isopropyl-(2E,4E,7S)-11-methoxy-3,7,11-trimethyl-2,4-dodecadienoate |
| 37. | (RS)-1-[3-chloro-4-(1,1,2-trifluoro-2-trifluoromethoxyethoxy)phenyl]-3-(2,6-difluorobenzoyl)urea |

TABLE II-continued

No. Chemical name (IUPAC)

38. 4-phenoxyphenyl (RS)-2-(2-pyridyloxy)propyl ether
39. (Z)-2-chloro-1-(2,4,5-trichlorophenyl)vinyl dimethyl phosphate
40. (EZ)-3-(2-chloro-1,3-thiazol-5-ylmethyl)-5-methyl-1,3,5-oxadiazinan-4-ylidene(nitro)amine In certain preferred instances, the toxicant is (E)-$N^1$-[(6-chloro-3-pyridyl)methyl]-$N^2$-cyano-$N^1$-methylacetamidine ("Compound A"). In other preferred instances, the toxicant is (EZ)—(RS)-1-methyl-2-nitro-3-(tetrahydro-3-furylmethyl) guanidine ("Compound B").

In certain instances, the toxicant is between 0.0001% to 20% by weight, such as about 0.0001% to about 5%. In certain instances, the range is about 0.001% to about 1%. In other instances, the range is about 0.01% to about 1%, such as 0.01% to 0.5%, i.e., 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, or 1.0%. In other instances, the amount is about 1%, 5%, 10%, 15% or 20%. In other instances, the insecticide is about 1%, 2%, 3%, 4%, 5%, 6%, 7%, 8%, 9%, 10%, 11%, 12%, 13%, 14%, 15%, 16%, 17%, 18%, 19% or 20% w/w. In other instances, the range the insecticide is present at 0.001% by weight to 5.0% by weight based on the weight of all components in the total composition, even more preferred is the range of 0.01% by weight to 1.0% by weight of all components in the total composition.

In certain instances, the composition of the present invention comprises an attractant. The attractant, can be a pheromone(s) or a feeding attractant(s) or combinations thereof. Pheromones are chemical substances produced by animals which serve as a stimulus to other individuals of the same species for one or more behavioral responses including, but not limited to, sex, food, aggregation or oviposition lures. A sex pheromone is broadly defined as a substance released by one member of a species to attract the opposite member for the purpose of mating. A large number of pheromones have been disclosed in U.S. Pat. No. 5,046,280 and U.S. Pat. No. 5,008,280, the contents of which in this respect are incorporated herein by reference. Where in the present invention it is desired to attract flies, the pheromone of choice is Z-9 Tricosene, tradename muscalure. Muscalure is produced by the female fly and can serve both as an aggregative and sex attractant. Those of skill in the art will know of other pheromones suitable for use in the present invention.

In addition, in certain aspects, one or more feeding attractants such as trimethylamine (TMA) is added, usually as the hydrochloride salt to replicate rotting flesh or fecal protein odors. In addition, in certain aspects, an indole is added which is a naturally-occurring substance also responsible in-part for fecal and other rotting protein odors. Indole and TMA have fly-attracting properties because their odors suggest a food source or medium suitable for egg propagation. In certain instances, the technology with regard to fly-attracting properties disclosed in U.S. Pat. No. 5,008,107 to Warner and incorporated herein by reference is used in the present invention.

In certain instances, the composition of the present invention comprises an attractant at a concentration of 0.001% to 20% by weight, such as about 0.001% to about 5%. In certain instances, the range is about 0.001% to about 1%. In other instances, the range is about 0.01% to about 1%, such as 0.01% to 0.5%, i.e., 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, or 1.0%.

Without being bound by any particular theory, it is believed that the toxicants have high bioavailability and are rapidly absorbed into the insect's body. As the bait kills flies with lower bait consumption, more flies are killed with less bait and therefore less toxicant. It is believed that a supersaturated solution of sugar solidifies and forms a glass-like coat when it dries on the granule. The attractants are first absorbed onto the core material, such as a porous core and then coated over top. The house fly pheromone is volatile, and the coating advantageously limits the amount of evaporation. Because the toxicant is substantially in the coating, the actual concentration that the fly receives when feeding is much higher than if it were spread throughout the entire bait. Advantageously, this increases the bait's toxicity and knockdown power but not to non-target birds or mammals.

In certain aspects, the toxicant is substantially in the coating. In still other aspects, when the composition further comprises an attractant, the attractant can be added to the inert core before the sugar layer and the sugar layer acts as a stability aid for the attractant.

In certain instances, more than 80% of the toxicant is in the coating, such as 80%, 81%, 82%, 83%, 84%, 85%, 86%, 87%, 88%, 89%, 90%, 91%, 92%, 93%, 94%, 95%, 96%, 97%, 98%, 99% or even 100% w/w.

III. Methods of Making

In another embodiment, the present invention provides a method for making the granular baits described herein. The methods are especially useful in coating irregularly shaped particles and provide a relatively uniform coating.

In certain embodiments, the process 100 set forth in FIG. 1 is used to make the insecticide baits of the present invention. In this process, water is heated (e.g., 80-120° C.) and sugar is added with agitation to produce a syrup such as a supersaturated solution 110. In certain instances, by heating the water and adding sugar (such as a sugar particle), the heated water contains more solute than room temperature water would contain and thus, the water is supersaturated. Optionally, a colorant can be added to the syrup. A toxicant 120 is then added to the supersaturated solution and heat is preferably maintained.

The inert core material is granulated in a mixer 125. In a separate vessel, as shown in step 130, an attractant and optionally a solubilizer (e.g., cremophor or other) are made into a premix. A solubilizer is an optional ingredient. Typical solubilizers may be hydrogenated castor oil known with the trade mark Cremophor from BASF. The preferred solubilizers include polyoxyl 40 hydrogenated castor oil, polyoxyl 35 castor oil, polyoxyethylene sorbitan fatty acid esters (polysorbates), poloxamers (Pluronics), and vitamin E-TPGS 1000, with the more preferred surfactant being Cremophor EL. Solubilizers and emulsifiers are typically only included for attractant compounds that are added as an emulsion (e.g., oil in water/water in oil). Those of skill in the art will know of other solubilizers suitable for use in the present invention.

In certain other instances, indole and TMA-HCl are solubilized in an alcohol such as ethanol and Z-9 tricosene is emulsified in the same mix at room temperature. This mixture is then added to the core and the coating subsequently applied. In another aspect, a pheromone is applied substantially free of other materials to the core material.

In step 135, the inert core material is mixed with the attractant premix until the attractant premixed is absorbed. In step 140, the supersaturated syrup having a toxicant is added to the mixer and mixed until a soft mass is formed.

In one aspect, a "soft mass" is a loose dough that turns to free flowing, coated granules because of both the temperature drop and the drying effect. Final granules may or may not need yet additional (mechanical or air) drying to produce a desired moisture content.

In certain instances, small quantities of fly attractant are added to the sugar syrup or core.

In certain instances, toxicants form a clear transparent solution in the supersaturated sugar syrup. In the "glaze coat," the toxicant(s) are dispersed in the sugar syrup.

In certain embodiments, the present invention provides a method for making a fly bait, the method comprising, consisting essentially of, or consisting of:

admixing a sugar syrup (e.g., such as a supersaturated sugar syrup) with a toxicant to produce a toxicant syrup;

granulating an inert core material;

optionally admixing an attractant with a solubilizer or solvent and emulsifier to produce a solution or an emulsion premix; and admixing the toxicant syrup and optionally the attractant premix with the granules to produce a coated granulated fly bait.

Advantageously, baits made using this process have reduced or substantially no dust. Typically, commercially available fly baits made via an extrusion or compression process have dust associated with the bait.

IV. Methods of Using

In another embodiment, the present invention provides a method for controlling flies, the method comprising, consisting essentially of, or consisting of:

applying a composition comprising:

an inert core material and a sugar layer comprising a supersaturated solution of sugar and a toxicant, which sugar solution binds to the core material and is dried on the inert core material, to a locus where fly control is needed or expected to be needed.

In certain aspects, flies can be filth flies such as house flies (*Musca domestica* Linneaus), bazaar flies (*Musca sorbens* (Weidemann)), eye gnats (*Hippelates* species), blow flies (Calliphoridae), little house flies (*Fannia* species), flesh flies (Sarcophagidae), and pomace flies (*Drosophila* species). In certain instances, the locus is selected from a farm, a cattle facility, a food processing facility, a restaurant, a recreational park, a residential area and a residential building. In certain instances, the locus is a cattle facility or an animal breeding facility.

Although the insect of particular interest is the fly, a skilled person will appreciate that the inventive composition and methods provided herein are useful for a variety of insects including, but not limited to, ants, roaches and crickets.

V. EXAMPLES

Example 1

Preparation of (E)-$N^1$-[(6-chloro-3-pyridyl)methyl]-$N^2$-cyano-$N^1$-methylacetamidine (Compound A) 0.5% Fly Bait A 500-gram batch of Compound A 0.5% fly bait was prepared using the following formula:

| Ingredients | wt % | Mass (g) |
| --- | --- | --- |
| Compound A Technical Grade (99.0%) | 0.51 | 2.55 |
| Corn Cob Granule | 64.81 | 324.05 |
| Sucrose Granulated Fine | 34.00 | 170.00 |
| Water for syrup | 8.50 | 42.50 |
| Trimethylamine HCl | 0.50 | 2.50 |
| Indole | 0.01 | 0.05 |
| Z-9-Tricosene | 0.08 | 0.40 |
| PEG-40 hydrogenated castor oil | 0.01 | 0.05 |
| FD & C Yellow #5 Powder | 0.05 | 0.25 |
| FD & C Yellow #6 Powder | 0.03 | 0.15 |
| Water for Emulsion | 0.90 | 4.50 |
| Total (water excluded) | 100.00% | 500.00 |

The bait was prepared according to the following procedure:

1. Preparation of 85% (w/w) Syrup: Water for the syrup was heated and sucrose was added until a clear syrup was obtained.
2. Colorant was added to the syrup.
3. Compound A was added to the syrup and particles were dispersed with a spatula. The syrup mixture was heated in a microwave oven until a clear syrup solution was obtained.
4. Preparation of Attractant Emulsion: Z-9 tricocene was mixed with indole, and the mixture was heated to obtain a clear solution. Cremophor was added.
5. Preparation of Fly Bait:
   i. Corn cob granules were charged to a mixer.
   ii. The attractant emulsion was added.
   iii. Trimethylamine HCl was added.
   iv. Compound A syrup was added to the mixer.
   v. A soft wet mass was formed and the mixer was turned to higher speed. With continued mixing, the soft mass turned into free-flowing granules.

Example 2

Preparation of (EZ)—(RS)-1-methyl-2-nitro-3-(tetrahydro-3-furylmethyl)guanidine (Compound B) 0.5% Fly Bait A 1000-gram batch of Compound B 0.5% fly bait is prepared using the following formula:

| Ingredients | wt % | Mass (g) |
| --- | --- | --- |
| Compound B Technical Grade 99.6% | 0.51 | 5.10 |
| Corn Cob Granule Maizorb 2 (#14/#20) | 64.81 | 648.10 |
| Sucrose Granulated Fine | 34.00 | 340.00 |
| Water for syrup | 9.1 | 91.00 |
| FD & C Yellow #5 | 0.05 | 0.50 |

-continued

| Ingredients | wt % | Mass (g) |
|---|---|---|
| FD & C Yellow #6 | 0.03 | 0.30 |
| Water for Emulsion | 0.90 | 9.00 |
| Total (water excluded) | 100.00% | 1,000.00 |

The bait is prepared according to the following procedure:
1. Preparation of 80% (w/w) Syrup: Water for the syrup is heated and sucrose is added until a clear syrup is obtained.
2. Colorant is added to the syrup.
3. Compound B is added to the syrup.
4. Preparation of Fly Bait.
    i. Corn cob granules are charged to a mixer.
    ii. Compound B syrup is added to the mixer.
    iii. A soft wet mass is formed. The soft mass is dried to form a free-flowing granule.

Example 3

Preparation of (E)-1-(6-chloro-3-pyridylmethyl)-N-nitroimidazolidin-2-ylideneamine 0.5% Fly Bait A 500-gram batch of (E)-1-(6-chloro-3-pyridylmethyl)-N-nitroimidazolidin-2-ylideneamine (Compound C) 0.5% fly bait is prepared using the following:

| Ingredients | wt % | Mass (g) |
|---|---|---|
| Compound C Technical Grade (99.0%) | 0.51 | 2.55 |
| Corn Cob Granule | 64.81 | 324.05 |
| Sucrose Granulated Fine | 34.00 | 170.00 |
| Water for syrup | 9.1 | 45.5 |
| FD & C Yellow #5 Powder | 0.05 | 0.25 |
| FD & C Yellow #6 Powder | 0.03 | 0.15 |
| Water for Emulsion | 0.90 | 4.50 |
| Total (water excluded) | 100.00% | 500.00 |

The bait is prepared according to the following procedure:
1. Preparation of 85% (w/w) Syrup: Water for the syrup is heated and sucrose is added until a clear syrup was obtained.
2. Colorant is added to the syrup.
3. Compound C is added to the syrup and particles are dispersed with a spatula. The syrup mixture is heated in a microwave oven until a clear syrup solution is obtained.
4. Preparation of Fly Bait:
    i. Corn cob granules are charged to a mixer.
    ii. Compound C syrup is added to the mixer.
    iii. A soft wet mass is formed. The soft mass is dried to form a free-flowing granule.

Example 4

Preparation of 0.5% Compound A Fly Bait

A 4-kg batch of Compound A 0.5% fly bait was prepared using the following formula:

| Ingredients | % W/W | Mass (g) |
|---|---|---|
| Compound A Technical Grade | 0.51 | 20.40 |
| Corn Cob Granule | 64.81 | 2,592.40 |
| Sucrose Granulated Fine | 34.00 | 1,360.00 |
| Water for syrup | 8.50 | 340.00 |
| FD & C Yellow #5 | 0.05 | 2.00 |
| FD & C Yellow #6 | 0.03 | 1.20 |
| Trimethylamine HCl | 0.50 | 20.00 |
| Water to dissolve TMA HCl | 0.50 | 20.00 |
| Indole | 0.01 | 0.40 |
| Z-9 Tricocene | 0.08 | 3.20 |
| Cremophor RH-40 | 0.01 | 0.40 |
| Water for Emulsion | 0.90 | 36.00 |
| Total (water excluded) | 100.00% | 4,000.00 |

The bait was prepared according to the following procedure:
1. Preparation of 80% (w/w) Syrup: Water for the syrup was and sucrose was added until a clear syrup was obtained.
2. Compound A was added to the syrup.
3. Preparation of Attractant Emulsion:
    i. Attractant pre-mix was prepared by mixing Z-9 tricocene with indole, and heating the mixture to obtain a clear solution. Cremophor was added.
    ii. Trimethylamine HCl was dissolved in an equal amount of DI water
4. Preparation of Fly Bait:
    i. Corn cob granules were charged to the mixer
    ii. trimethylamine HCl solution was added.
    iii. The attractant emulsion was added to the mixer.
    iv. Compound A syrup was added to the mixer.
    v. A soft wet mass formed, and mixing was continued until the wet mass turned into a free-flowing granular product.

Example 5

Field Testing of Granular Fly Bait

This experiment was a pair-wise comparison in a field-use situation at a commercial boarding stables of a commercially available fly bait, QuickBayt (0.5% Compound C, 0.1% Z-9 tricosene, EPA Reg. No. 11556-137), vs an inventive fly bait having equivalent active ingredients (0.5% Compound C, 0.1% Z-9 tricosene;), but made as a coated corn-cob grit granule ("TEST"). The test set-up was a five-replicate, equidistant tray, alternating bait protocol in a W-E linear transect along the south side of an open-sided horse barn. Each bait station consisted of a 12"×12"×2" metal mesh bird exclosure into which was inserted a cardboard tray. Stations were separated by seven foot intervals, baited with three grams of bait each, and exposed to flies for approximately six hours.
Test Substance:
Formulated granular fly bait, orange in color was prepared by the methods herein by coating corn cob grits with a supersaturated sucrose solution containing the toxicant; hereinafter referred to as "INVENTIVE."

| Active Ingredients: | |
|---|---|
| Compound C | 0.50% |
| Z-9 tricosene (CAS No. 27519-02-4) | 0.10% |

Control Substance:
QuickBayt fly bait, a red colored, extruded granular bait, EPA Reg. No. 11556-137, hereinafter referred to as "QuickBayt."

| Active Ingredients: | |
| --- | --- |
| Compound C | 0.50% |
| Z-9 tricosene (CAS No. 27519-02-4) | 0.10% |

Table III lists individual tray counts and total counts. The INVENTIVE bait performed four times as well as Quick-Bayt, "winning" all replicates (mean rank score of 1.0), even though the active ingredient identity and nominal concentrations were the same for both baits. House flies (*Musca domestica* L.) were the only dipteran species present in the trays at counting.

TABLE III

| POSITION | BAIT | HOUSE FLIES | RANK |
| --- | --- | --- | --- |
| 1 | QuickBayt | 0 | 2 |
| 2 | INVENTIVE | 9 | 1 |
| 3 | INVENTIVE | 20 | 1 |
| 4 | QuickBayt | 4 | 2 |
| 5 | INVENTIVE | 11 | 1 |
| 6 | QuickBayt | 2 | 2 |
| 7 | INVENTIVE | 35 | 1 |
| 8 | QuickBayt | 12 | 2 |
| 9 | INVENTIVE | 17 | 1 |
| 10 | QuickBayt | 5 | 2 |
| TOTAL | QuickBayt | 23 | 2.0 |
| TOTAL | INVENTIVE | 92 | 1.0 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A composition for killing flies, said composition comprising:
   an inert core material;
   a sugar layer comprising a supersaturated solution of sugar, wherein said supersaturated solution of sugar is between 65 and 95% w/v, wherein said sugar is a member selected from the group consisting of sucrose, fructose, lactose, and sorbitol;
   a toxicant, which coats said inert core material and is dried on the core material, wherein the toxicant is within the sugar layer, wherein the supersaturated solution of sugar solidifies and forms a glass-like coat, wherein said toxicant is a member selected from the group consisting of (E)-$N^1$-[(6-chloro-3-pyridyl)methyl]-$N^2$-cyano-$N^1$-methylacetamidine, (EZ)—(RS)-1-methyl-2-nitro-3-(tetrahydro-3-furylmethyl)guanidine and (E)-1-(6-chloro-3-pyridylmethyl)-N-nitroimidazolidin-2-ylideneamine; and
   an attractant selected from the group consisting of a pheromone or a feeding attractant, wherein the attractant is added to the inert core before the sugar layer and wherein the sugar layer acts as a stability aid for the attractant.

2. The composition of claim 1, wherein said inert core material is a member selected from the group consisting of cellulose granules, ground nut hulls, saw dust, clay pellets, a polymer, sand, a grain, a seed, millet, milo, oat bran, corn part, crack rice, crack wheat, couscous, *quinoa*, and steel cut grain.

3. The composition of claim 2, wherein said inert core material is a grain.

4. The composition of claim 2, wherein said inert core material is a seed.

5. The composition of claim 4, wherein said seed is selected from the group consisting of a chia seed, a sesame seed, a flax seed, and an amaranth seed.

6. The composition of claim 2, wherein said core material is a corn part.

7. The composition of claim 6, wherein said corn part is selected from the group consisting of corn grit, corn cob grit and cracked corn.

8. The composition of claim 7, wherein said corn part is corn cob grit.

9. The composition of claim 1, wherein said supersaturated solution of sugar is between 65 to 85% weight per volume.

10. The composition of claim 1, wherein said sugar is sucrose.

11. The composition of claim 1, wherein said toxicant is (E)-$N^1$-[(6-chloro-3-pyridyl)methyl]-$N^2$-cyano-$N^1$-methylacetamidine.

12. The composition of claim 1, wherein said toxicant is (EZ)—(RS)-1-methyl-2-nitro-3-(tetrahydro-3-furylmethyl)guanidine.

13. The composition of claim 1, wherein said toxicant is (E)-1-(6-chloro-3-pyridylmethyl)-N-nitroimidazolidin-2-ylideneamine.

14. The composition of claim 1, wherein said toxicant is between 0.0001% to 20% by weight of the composition.

15. The composition of claim 1, wherein said toxicant is between about 0.0001% to about 5% by weight of the composition.

16. The composition of claim 1, wherein said toxicant is between about 0.001% to about 1% by weight of the composition.

17. The composition of claim 1, wherein said toxicant is between 0.01% to 0.5% by weight of the composition.

18. The composition of claim 1, wherein the attractant is a pheromone.

19. The composition of claim 18, wherein said pheromone is Z-9 tricosene.

20. The composition of claim 1, wherein the sugar is sorbitol.

21. A method for controlling flies, said method comprising applying a composition according to claim 1, to a locus where fly control is needed or expected to be needed, to thereby control flies.

22. The method of claim 21, wherein said flies are selected from the group consisting of house flies (*Musca domestica* Linneaus), bazaar flies (*Musca sorbens* (Weidemann)), eye gnats (*Hippelates* species), blow flies (Calliphoridae), little house flies (*Fannia* species), flesh flies (Sarcophagidae), and pomace flies (*Drosophila* species).

23. The method of claim 21, wherein said locus is selected from the group consisting of a farm, a cattle facility, a food processing facility, a restaurant, a recreational park, a residential area and a residential building.

24. The method of claim 23, wherein said locus is an animal breeding facility.

* * * * *